United States Patent [19]
Young et al.

[11] Patent Number: 6,063,617
[45] Date of Patent: May 16, 2000

[54] ON-LINE RESPIROMETER USING CONSTANT OXYGEN CONCENTRATION IN REACTION VESSEL

[75] Inventors: James C. Young, Springdale; Mark L. Kuss, Lowell, both of Ark.

[73] Assignee: Challenge Enviromental Systems, Inc., Fayetteville, Ark.

[21] Appl. No.: 09/146,846

[22] Filed: Sep. 3, 1998

[51] Int. Cl.$^7$ .................................................. C12M 3/00
[52] U.S. Cl. .................................. 435/287.5; 435/286.6; 422/79; 436/62
[58] Field of Search .............................. 422/79; 366/101, 366/102; 435/287.1, 287.5, 286.6; 436/62

[56] References Cited

U.S. PATENT DOCUMENTS

| | | | |
|---|---|---|---|
| 3,731,522 | 5/1973 | Mikesell ........................................ | 73/19 |
| 4,783,172 | 11/1988 | Garg .......................................... | 366/142 |
| 4,947,339 | 8/1990 | Czekajewski et al. .................. | 364/497 |
| 5,125,262 | 6/1992 | Garg .......................................... | 73/19.12 |

OTHER PUBLICATIONS

"Bioscan Continuous Toxicity Monitor–System Overview" N–CON Systems Co. Inc.
"Respirometer—Basic, Extra & Advanced Models" Spec. Sheet Minworth Systems Ltd.—Oct. 1991.
"RODTOX—The Instrument for the On–Line Determination of the BOD & Toxicity of Municipal & Industrial Wastewaters" KELMA.
"Bio Monitor BOC Measuring System" LAR Analytik & Umwelt Messtechnik GMBH.
"BIOX–1010" Technical Specifications STIP Siepmann und Teutscher GmbH.

*Primary Examiner*—David A. Redding
*Attorney, Agent, or Firm*—Stephen D. Carver

[57] ABSTRACT

An on-line respirometer for measuring oxygen uptake by wastewater samples, plants, or animals due to respiration. A closed reaction vessel is adapted to receive and expel wastewater samples or the like. The vessel contains oxygen-sensing probes that constantly evaluate the concentration of oxygen either in the headspace of the vessel or in the samples contained in the slurry within the vessel. The oxygen that is consumed during the respiration of the test samples is immediately replaced by concurrent oxygen injection to maintain a constant oxygen concentration in the reaction vessel. This rapid oxygen replacement is accomplished through an oxygen feedback supply circuit that restores oxygen concentration to its original level in a matter of seconds. The respirometer uses a constant air flow system that allows for the precise oxygen level control. Direct measurement of the oxygen injected for equilibrium control is equated to the uptake.

27 Claims, 2 Drawing Sheets

ON-LINE RESPIROMETER USING CONSTANT OXYGEN CONCENTRATION IN REACTION VESSEL

BACKGROUND OF THE INVENTION

I. Field of the Invention

The present invention relates generally to respirometers. More particularly, the present invention relates to an on-line respirometer system and methods in which oxygen consumption by microorganisms, plants, or animals is measured by determining and monitoring the amount of injection oxygen required to maintain a constant concentration. Known prior art devices are found in United States Patent Class 366, Subclasses 101 and 102.

II. Description of the Prior Art

It has long been recognized by those skilled in the art that water contains a limited amount of oxygen. It is well known that respiring microorganisms, plants, or animals reduce oxygen concentrations within a given volume. Respirometers can monitor these biological reactions by measuring an exchange of gases, usually oxygen, carbon dioxide, or in the case of anaerobic reactions, methane. Such instruments have been used widely for assessing the response of microorganisms in wastewater treatment processes. The reduction in oxygen concentration is directly proportional to the amount of biodegradable organic matter available in wastewater.

A number of recent respirometers have been designed for on-line operation. These respirometers measure oxygen uptake or gas production in a continuous or semi-continuous mode. These measurements allow long-term changes in biological reactions to be monitored and recorded. Common applications of these prior art respirometers include monitoring oxygen uptake in wastewater treatment processes, monitoring the effect of changes in wastewater composition, and identifying the presence of toxic inputs that can adversely affect wastewater treatment processes.

Various respirometer designs are known in the art. Prior art respirometers typically comprise a reaction vessel, some method for introducing test wastewater, and a suitable device for monitoring the pressure change in the reaction vessel. The wastewater is introduced within the vessel along with microorganisms. The microorganisms grow and degrade the contaminants in the wastewater, thereby consuming oxygen and reducing oxygen concentration. Oxygen consumption is assumed to be the principal cause of pressure change within the reaction vessel. The reduction in oxygen is indicated by the pressure change in the reaction vessel over time.

There are four types of on-line respirometers available for commercial application. Type I on-line respirometers utilize a semi-continuous measuring method. These devices measure the change in dissolved oxygen concentration contained in a mixture of wastewater and microorganisms or the change in pressure within the respirometer. A long-term record of oxygen uptake is accomplished by conducting repetitive batch tests. In Type I respirometers an operator introduces a microorganism slurry along with a wastewater sample into the reaction vessel, adds oxygen, aerates for a short period of time, and finally measures the decrease in dissolved oxygen (DO) concentration or pressure drop. This difference between the initial and final dissolved oxygen concentrations or pressure drop corresponds to the amount of oxygen consumed by the microorganisms for the stabilization of the organic material present in the wastewater. The foregoing procedure is repeated several times and the results are plotted on a graph.

The latter procedure is represented by the following formula:

$$DO = DO_0 - \int R_s dt - \int R_m dt, \text{ mg/l, where:}$$

$DO$=Dissolved oxygen concentration in the sample at any time after beginning the test, mg/L $DO_0$=Dissolved oxygen concentration in the test sample at the beginning of the test, mg/L $R_s$=Rate of oxygen uptake resulting from substrate (waste) oxidation, mg $O_2$/l-hr $R_m$=Rate of oxygen uptake resulting from respiration of the microorganisms, mg $O_2$/l-hr The resulting measurement may be represented as the oxygen uptake rate (OUR), expressed in terms of mass of oxygen per liter of mixture per hour (mg $O_2$/L-hr), or as the specific oxygen uptake rate (SOUR). In the SOUR test, the rate of oxygen consumption is expressed as the mass of oxygen per unit of microorganism mass, M, per hour (g. $O_2$/g M/hr), or $OUR = R_s + R_m$, mg $O_2$/L-hr $SOUR = R_s/M + R_m/M$, mg $O_2$/g. M-hr Recording and plotting maximum OUR or SOUR versus time for successive batch tests creates a continuous presentation of responses to factors affecting microorganism growth. These factors include changes in waste concentration, composition, or toxicity as reflected by oxygen uptake rates. Knowledge of the background rate of respiration, Rm, allows calculation of the rate of oxidation, Rs, of the organic constituents of the wastewater sample. One problem with Type I respirometers is that the wastewater often must be diluted with aerated water before the measurement can take place. Another disadvantage is that the operation is limited to sequential batch reactions so that they do not provide a true record of continuous oxygen uptake. The oxygen uptake also can be measured by a manometric method, that is, by measuring the decrease in pressure within a sealed vessel containing the microorganisms and wastewater or by a decrease in the oxygen content of the head space gas.

In Type II on-line respirometers, the microorganism sample is mixed with air or oxygen enriched air within the reaction vessel during operation so that the dissolved oxygen concentration remains relatively constant. When a wastewater sample is added, the dissolved oxygen concentration temporarily begins to decrease in response to biodegradation in much the same manner as in Type 1 respirometers. However, in Type II respirometers the reduced dissolved oxygen concentration begins to increase as the rate of oxygen transferred into the culture medium exceeds the rate of oxygen uptake. The resulting dissolved oxygen curve is termed a "respirogram". A mass balance of dissolved oxygen concentration and mass transfer can be expressed in summary form as follows:

$$DO_t = DO_0 - \int R_s dt - \int R_m dt + \int K_{La}(DO_s - DO_t) dt, \text{ mg/L,}$$

where:

$K_{La}$=Oxygen mass transfer coefficient $DO_s$=Saturation value for dissolved oxygen under current test conditions, mg/L $DO_t$=Dissolved oxygen concentration at any time, t, after addition of wastewater, mg/L By measuring the dissolved oxygen concentration over time and using predetermined values for the microbial respiration and mass transfer reactions, the above equation may be used to calculate the oxygen uptake attributable to the biodegradation of wastewater constituents in the wastewater sample injected at the beginning of the test. The resulting mass of oxygen uptake is defined as the "short time biochemical oxygen demand", or $BOD_{ST}$. A plot of successive measures of $BOD_{ST}$ indicates the change in wastewater quality over time. A plot of the oxygen uptake rate occurring immediately after the injection of wastewater sample, adjusted for microorganism respiration and mass transfer, gives a measure of maximum OUR. Several distinct disadvantages are associated with such respirometers. One disadvantage is the large number of repetitive measurements required to obtain a meaningful indication of wastewater quality. Another disadvantage is that the results are dependent on the mass transfer characteristics, which are subject to considerable variability over time.

In Type III on-line respirometers, oxygen uptake is measured as the decrease in dissolved oxygen concentration across a closed vessel that continuously receives a mixture of wastewater and microorganisms. Alternatively the microorganisms may be maintained within the vessel on a solid or semi-solid support medium. A decrease in dissolved oxygen concentration occurs almost immediately in response to changes in wastewater quality or composition. This approach provides a continuous measure of oxygen uptake rate that can be expressed as follows:

$$OUR = \Delta DO * R_w / V, \text{ mg/L-hr},$$

where:
$\Delta DO$=difference in dissolved oxygen concentration across reactor, mg/L
V=Volume of reactor, L
$R_w$=Rate of wastewater inflow into the reaction vessel, L/hr The data also may be processed to produce a measure of short term BOD ($BOD_{ST}$). The $BOD_{ST}$ is obtained by correlating the oxygen uptake rate to standard measure of biochemical oxygen demand. Alternatively $BOD_{ST}$ may be calculated by comparison to the oxygen uptake of a synthetic substrate having a known BOD. One disadvantage of Type III respirometers is that the decrease in oxygen concentration across the reaction vessel must be relatively large to give an accurate measure of oxygen uptake. Another disadvantage of Type III systems that maintain a fixed medium is that the attached microorganisms may respond differently from those in the wastewater.

A Type IV on-line respirometer receives wastewater and microorganisms as in the Type III system but in an enclosed vessel having a defined headspace volume. Air is pumped into the headspace volume at a controlled rate and the resulting change in oxygen content of the gas phase is used as a measure of oxygen uptake rate as follows:

$$OUR = K_a (\Delta\%O) R_a / V, \text{ mg/L-hr},$$

where
$K_a$=units coefficient
$\Delta\%O$=change in oxygen content of the headspace gas from gas inlet to outlet, %
$R_a$=Rate of air flow into the unit, L/hr
V=Volume of culture slurry A specific disadvantage of Type IV respirometers is that the change in oxygen content of the air stream must be relatively large to provide an accurate measure of oxygen consumption by the microorganisms.

The known prior art respirometers are based on the principle of difference of dissolved oxygen in the culture slurry or headspace oxygen content or pressure existing within the reaction vessel over time due to consumption of oxygen by microorganisms in the contained sample. All known prior art respirometers require relatively large changes in dissolved oxygen concentration or headspace oxygen content to provide precise and accurate measurements of oxygen uptake of the test wastewater.

We have found it desirable to depart from the conventional techniques listed above. In our invention, oxygen uptake is determined directly by measuring the amount of oxygen that must be injected into a respirometer vessel to maintain an essentially constant dissolved oxygen concentration in the culture slurry or a near constant oxygen content in the headspace gas above the sample. The injection of oxygen is made in response to minute changes of oxygen in the containment vessel using oxygen concentration sensors within the vessel linked to suitable feedback computational devices.

SUMMARY OF THE INVENTION

The methods and apparatus described herein measure oxygen uptake within a system comprising a slurry sample confined below a gaseous headspace within a closed reaction vessel. Oxygen uptake may be determined by feeding pure oxygen to the reaction vessel in response to very small changes in headspace oxygen concentration, thereby maintaining a near constant oxygen percentage in the headspace gas in contact with the culture slurry. Alternatively, oxygen uptake may be determined by monitoring the amount of oxygen feed needed to maintain a constant dissolved oxygen concentration in the culture slurry.

The amount of oxygen required to maintain a constant dissolved oxygen concentration or headspace composition in the vessel, adjusted for minor differences in the oxygen content of the inlet and outlet air and water streams, is substantially equal to the consumption of oxygen by microorganisms in the culture slurry. Microorganisms use oxygen for biodegrading organic contaminants in the wastewater. As microbial cells respire, oxygen is consumed by this respiration and the dissolved oxygen concentration in the culture slurry begins to decrease. When a dissolved oxygen probe detects a small decrease in dissolved oxygen concentration, an amount of oxygen equal to that consumed is replaced by means of a detection circuit and feedback control system. Preferably the system comprises an injection valve that is modulated via computer in response to a signal from the dissolved oxygen probe. In this manner dissolved oxygen concentrations and headspace gas can be controlled to maintain oxygen levels within less than 1% of their preset values. Because microorganisms are not adversely affected when growing in an oxygen environment above 1 mg/L and below about 40 mg/L, oxygen uptake rates are not affected adversely by maintaining a dissolved oxygen level between these concentrations.

In the best mode a low rate stream of air or oxygen-enriched air is pumped through the vessel headspace at a controlled rate to flush out waste carbon dioxide and other non-oxygen gases. Because the oxygen content of the exhaust gas is the same as that in the headspace gas, the flushing system contributes essentially no error to the oxygen uptake measurements. The amount of oxygen required to maintain a constant supply in the headspace gas equals the amount of oxygen transferred to the culture slurry in response to consumption of oxygen by microorganisms. This relationship is represented mathematically as follows:

$$OUR=R_o,$$

and $$R_o=R_s+R_m+(DO_{in}-DO_{out})q_w/V+k(O_{2in}-O_{2out})q_a/V \text{ in units of mg. } O_2/L\text{-hr},$$

where, $DO_{in}$=dissolved oxygen concentration in the influent wastewater microorganism slurry;

$DO_{out}$=dissolved oxygen concentration in culture discharge stream;

k=units coefficient;

$O_{2in}$=percent oxygen in influent flushing gas stream;

$O_{2out}$=percent oxygen in effluent flushing gas stream;

$q_w$=liquid waste flow rate;

$q_a$=flow rate of flushing air into system;

$R_o$=the rate of oxygen input necessary to maintain a constant dissolved oxygen concentration or headspace oxygen content;

$R_s$=Rate of oxygen uptake due to substrate (waste) oxidation, mg $O_2$/1-hr., and, $R_m$=Rate of oxygen uptake due to microorganism respiration, mg $O_2$/1-hr.

In most cases, the difference in oxygen content of the influent and effluent air and water streams is sufficiently small that it can be ignored. However these parameters can be included in the system mathematical model to improve the accuracy and precision obtained with oxygen uptake measurements.

When operating in a batch or semi-continuous mode, the rate at which oxygen is added to the reaction vessel, and therefore consumption, is processed by mathematical models as described above to produce measures of OUR, SOUR, or $BOD_{st}$. The respirometer may also be used to produce a direct measure of oxygen uptake rate during continuous operation.

Thus a basic object of the invention is to provide a respirometer that directly measures oxygen injection rates to determine oxygen uptake, rather than measuring oxygen depletion in the culture slurry or headspace gas within the culture vessel.

Another basic object is to provide a respirometer as described that maintains a near-constant oxygen pressure or concentration. It is a feature of this invention that a unique feedback control circuit is employed to maintain equilibrium.

Another important object is to provide a respirometer than quickly replaces consumed oxygen in response to a signal from a dissolved oxygen probe or gas phase oxygen sensor.

Another object is to provide a respirometer that allows operation at a user-selected dissolved oxygen concentration or headspace oxygen content.

Another important object is to monitor oxygen uptake by a culture of microorganisms in a respirometer that is designed to operate in a batch, semi-continuous, or continuous mode.

Another basic object is to provide a respirometer as described where the oxygen uptake measurement is independent of other gases in the headspace, such as nitrogen and carbon dioxide.

Another important object of the invention is to maintain oxygen concentration high enough so that the rates of waste biodegradation and microorganism respiration are not adversely affected by lack of available oxygen.

A related object is to provide a respirometer than can maintain any dissolved oxygen concentration between 1 and 40 mg/L.

Another object is to provide a respirometer of the character described that accommodates headspace oxygen contents ranging from 5 to 95% by volume.

A related object is to provide a respirometer that is well suited for routine wastewater analysis.

Another object is to provide a respirometer of the character described that can measure the oxygen uptake by living organisms such as plants, insects, fish and other animals.

These and other objects and advantages of the present invention, along with features of novelty appurtenant thereto, will appear or become apparent in the course of the following descriptive sections.

BRIEF DESCRIPTION OF THE DRAWINGS

In the following drawings, which forms a part of the specification and which are to be construed in conjunction therewith.

DETAILED DESCRIPTION OF THE INVENTION

Figure 1:
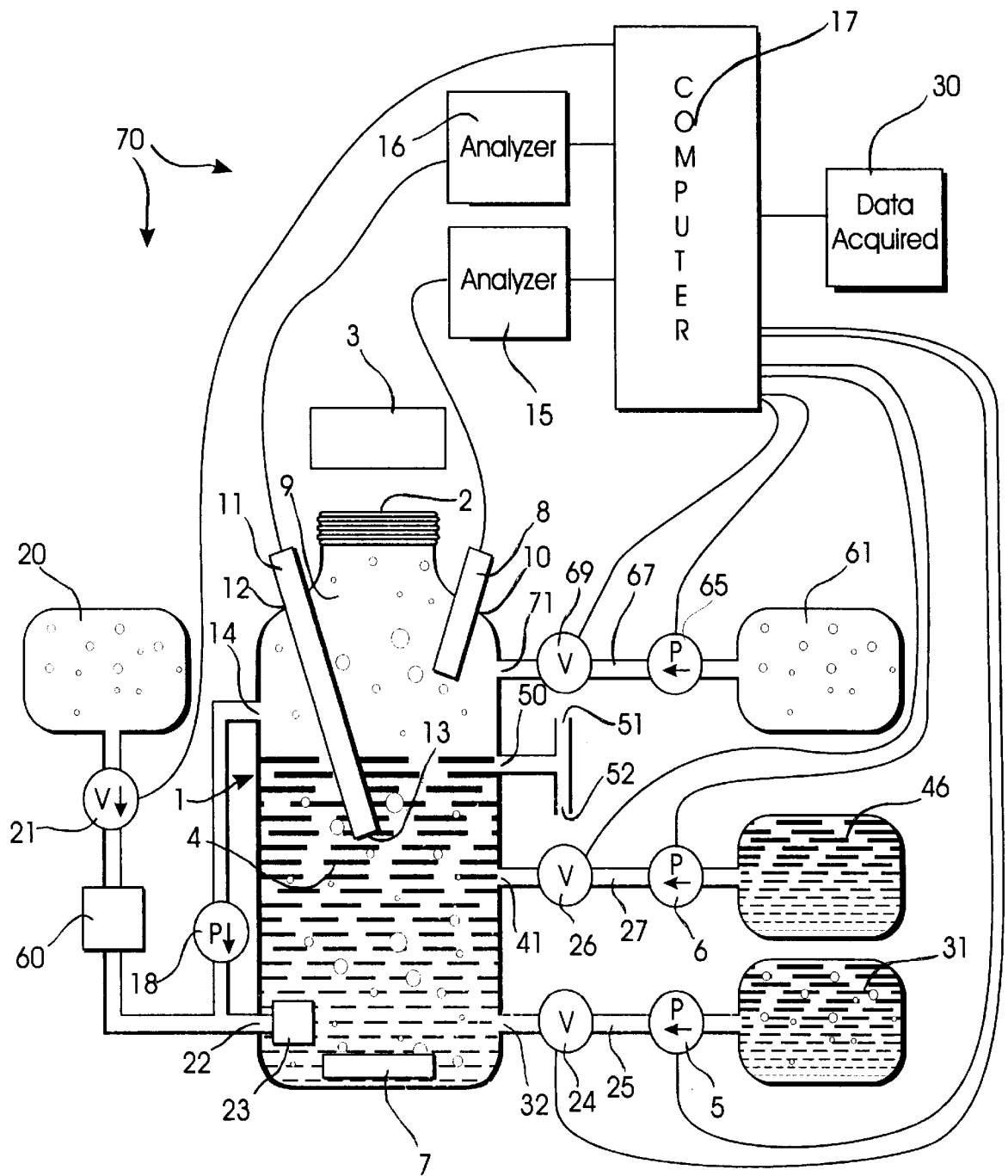
FIG. 1 is a diagrammatic view of the best mode of our system.

An on-line respirometer 70 according to the best mode of the invention is illustrated in the accompanying drawing. Respirometer 70 preferably comprises a reaction vessel 1 having an opening 2 and a cover 3. An aqueous culture of microorganisms 31 is added to the vessel either manually through opening 2, or is pumped into the vessel using pump 5 through port 32, valve 24, and line 25. A wastewater sample 46 is added manually through opening 2 or is pumped into the vessel through port 41 using pump 6, line 27 and valve 26. The respiring sample, comprising a mixture of microorganisms and wastewater, becomes culture slurry 4. Alternatively, the respiring sample may comprise samples of plants, animals, soils, inorganic substances, or any other substance or composition of matter that consumes oxygen.

Agitation of the culture slurry 4 is preferred. Agitation may be provided through a magnetic stirring device using magnet 7, or by recycling headspace gases through port 14, via pump 18, and diffuser 23. (Both agitation processes may occur simultaneously). Where the respiring sample comprises samples of plants, animals, soils, inorganic substances, etc., agitation has been found unnecessary.

Oxygen uptake is equal to the amount of oxygen required to maintain a constant dissolved oxygen concentration in slurry 4 or oxygen content of headspace gas 9. In one embodiment, oxygen sensor 8 is inserted into the headspace gas 9 through port 10. In another embodiment, a dissolved oxygen probe 11 is inserted through port 12 and tip 13 is submerged in the slurry 4. A suitable dissolved oxygen probe is available from Yellowstone Instruments. An ideal headspace oxygen sensor is available from the Figaro Company.

In yet another embodiment, oxygen sensor 8 and dissolved oxygen probe 11 are included simultaneously.

Oxygen sensor 8 and probe 11 are connected to analyzers 15 and 16. Signals from analyzers 15 and 16 containing oxygen concentration information are passed electronically to a system control computer 17. Suitable control software is an industry standard package, sold under the trade name "HP VEE" by the Hewlett Packard Company. The data acquisition software is essentially the same as that used in prior art, non-continuous, batch-type respirometers, such as that based upon U.S. Pat. No. 5,092,181, which is hereby incorporated by reference.

The preferred system further comprises an oxygen source 20 connected to reaction vessel 1 through valve 21, flow measuring device 60, port 22, and inlet diffuser 23. Oxygen source 20 can consist of gaseous oxygen from a pressurized tank, an electrolytic cell, or a hydrogen peroxide solution that is converted biologically to gaseous oxygen when brought into contact with microorganisms. The system control computer 17 is connected to valve 21 of the oxygen supply circuit. It is also connected to valve 24, and pump 5 in culture inlet line 25, and to valve 26 and pump 6 in wastewater input line 27. Computer 17 is additionally connected to data acquisition computer 30.

When operating in the batch mode, microorganisms are added manually from culture 31 or through port 32 via pump 5, line 25 and valve 24. Oxygen is added through port 22 and diffuser 23 via source 20, valve 21 and meter 60 until the dissolved oxygen concentration in slurry 4 is at a preselected level. Wastewater from source 46 is then added in a predetermined volume to the vessel 1, either manually through opening 2 or through port 41 via pump 46, valve 6 and line 27 until the desired wastewater-to-microorganism ratio is achieved in slurry 4. Oxygen uptake is then measured as the amount of oxygen needed to keep a constant dissolved oxygen concentration or constant headspace oxygen content as the microorganisms in slurry 4 degrade the constituents of the wastewater.

The semi-continuous mode consists of sequential batch operation. The contents of the reaction vessel 1 are removed and replaced intermittently with new aliquots of culture 31 and wastewater 46 with subsequent measure of oxygen uptake as described for batch tests. Data is processed and successive measurements of OUR, SOUR or $BOD_{st}$ are plotted.

In the continuous mode, microorganisms from culture 31 are added to reaction vessel 1 through pump 5, line 25, valve 24 and port 32. Wastewater 46 is added by pump 6 to the reaction vessel 1 through line 27, valve 26, and port 41 to produce a desired ratio of waste input to microorganism mass in culture slurry 4. As the microorganisms in slurry 4 oxidize organic or inorganic contaminants in wastewater sample 46, oxygen is consumed through synthesis and respiration reactions, resulting in a small depletion of the dissolved oxygen concentration in slurry 4 and headspace gas 9. Sensor 8, probe 11 or both detect this small depletion, and signals are passed by analyzers 15 and 16 to control computer 17.

Computer 17 in turn generates a signal that causes oxygen control valve 21 to open and admit a sufficient amount of oxygen through flow meter 60 into slurry 4 to increase the dissolved oxygen concentration in slurry 4 to a preset level. Oxygen levels in culture slurry 4 can be set at any concentration between 1 and 40 mg/L of dissolved oxygen or 5 to 95% oxygen in the headspace gas 9 by controlling the oxygen content of air input 61. The culture 31 and wastewater 46 mixture exits reaction vessel 1 through exit port 50 and outlet fitting 53 during continuous operation or during changes in batch inputs. Outside air 61 may be added to the reaction vessel through port 71 via pump 65, line 67, and valve 69 to remove excess carbon dioxide and other inert gasses. Oxygen enriched air may be used to maintain a desired oxygen content in the headspace gas 9 ranging from 5 to 95% oxygen. Excess air in the headspace gas 9 exits through port 50 and fitting 51.

EXAMPLE 1

Figure 2:
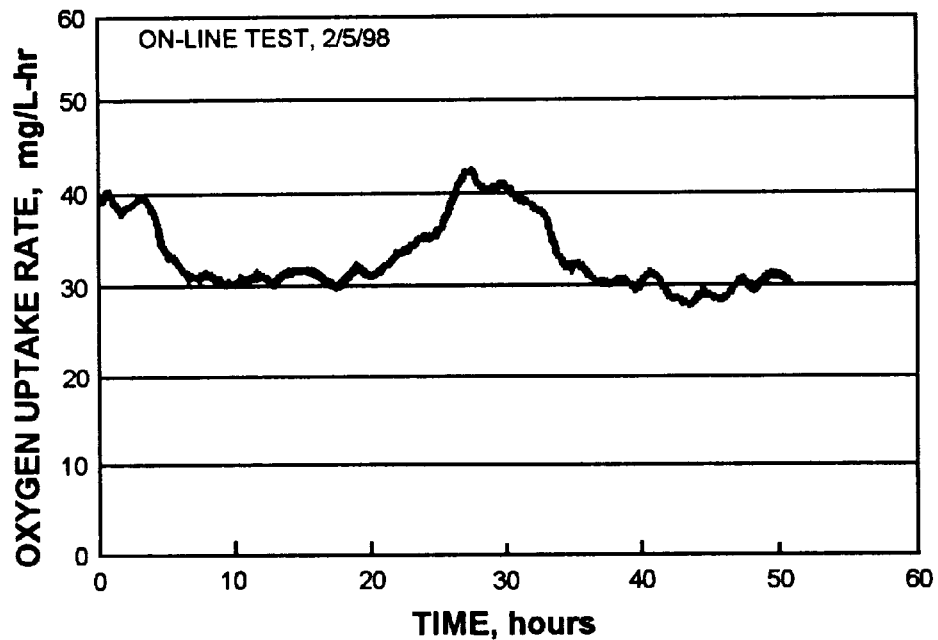
FIG. 2 is a graph of the results of a continuous test with wastewater discussed in conjunction in Example 1; and, FIG. 3 is a graph of the results of a sequential batch test discussed in conjunction with Example 2.

An example of the method and apparatus stated above can be seen in the uptake of oxygen for a sample of synthetic wastewater. Results from a continuous test are shown in FIG. 2. In this case, wastewater was dosed to the reactor using pump 6 along with a culture pumped from a laboratory-scale reactor using pump 5. Agitation of the sample was achieved by recycling headspace gases through pump 18 and diffuser 23. Oxygen uptake rates ranged from about 28 to 42 mg./L-hr. The occurrence of an increase in organic content of the wastewater stream can be seen around hour 25 when the oxygen uptake rate began to increase and eventually peaked at about 28 hours. Correlation of these measurements to a standard test substance can be used to produce a measure of short-term BOD of the sample. Field calibration would be used in full-scale applications to achieve the proper relationship between wastewater load and treatment plant operation.

EXAMPLE 2

Figure 3:
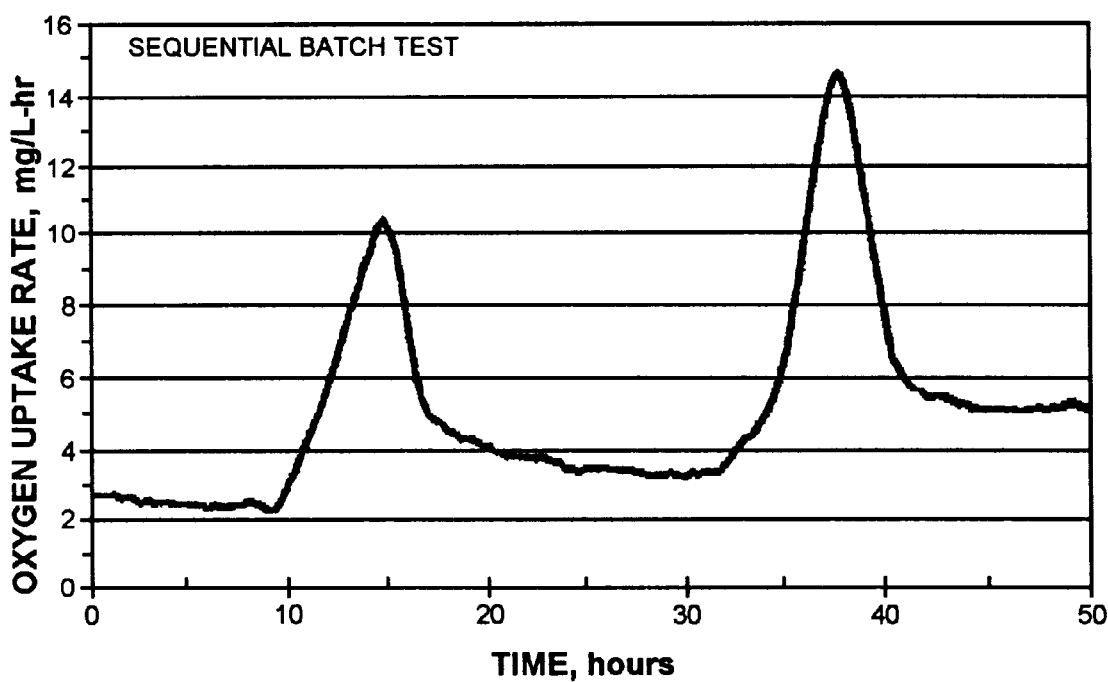

A sequential batch test is shown in FIG. 3. In this case, two doses of approximately 125 mg of synthetic wastewater were injected into the reaction vessel that contained an active microorganism culture. One dose occurred at 10 hours, the second at 36 hours. Each dose of wastewater showed a rapid increase in oxygen uptake followed by a return to endogenous rate within 6 to 10 hours. Field calibration would be used in full-scale applications to achieve the proper relationship between wastewater load and treatment plant operation.

EXAMPLE 3

The method and apparatus of the invention can be used for assessing the oxygen uptake of small animals such as mice or insects by placing the animal in the respirometer vessel on a bed of dry material that will absorb liquid wastes and provide the proper test environment in terms of temperature, light, oxygen content, etc. Oxygen uptake would be measured using the same procedure as with liquid wastewater samples except that the slurry will be replaced by a dry environment and no mixing of the sample is required. Headspace gases will be recycled to provide uniform contact of oxygen to the respiring sample.

EXAMPLE 4

The method and apparatus of the invention can be used for assessing the oxygen uptake of small swimming animals such as fish or *Daphnia magna*, a small water flea. These organisms would be placed within the test vessel in water that provides the proper test environment in terms of temperature, light, oxygen content, etc. Oxygen uptake would be measured using the same procedure as with liquid wastewater samples except that the slurry will be replaced by the water containing the subject organism. The headspace gases will be mixed by the recycle of headspace gas through the recycle pump. Mixing of the water containing the test organisms will be mixed by agitation with the recycled headspace gas.

EXAMPLE 5

The method and apparatus of the invention can be used for assessing the oxygen uptake of a solid sample such as a contaminated soil sample from a refinery site or a compost sample from a composting operation. The soil sample would be placed within the test vessel in a manner that provides the proper test environment in terms of temperature, light, oxygen content, etc. Oxygen uptake would be measured using the same procedure as with liquid wastewater samples except that the slurry will be replaced by the soil sample. In this case, the sample would not be agitated but headspace gases would be mixed by recycling headspace gas through pump 18 or by pumping headspace gas through the porous sample using pump 18 and diffuser 23.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense. In particular, it is within the scope of the invention to measure the oxygen uptake by living organisms including plants, insects, fish and other animals.

What is claimed is:

1. An on-line respirometer comprising:
   a reaction vessel for simultaneously containing a slurry and headspace gases, the slurry sample comprising a mixture of a microorganism culture and either wastewater or a chemical solution;
   means for continuously delivering a flow of microorganisms into said vessel;
   means for continuously delivering a flow of wastewater or chemical solution into said vessel;
   flushing means for establishing a predetermined mixture of headspace gases and for purging undesirable gases from said headspace;
   venting means for discharging headspace gases in response to said flushing means and for discharging slurry in response to said wastewater or chemical solution delivery means;
   sensor means for determining the concentration of oxygen in said headspace gases or said slurry sample;
   an external source of oxygen for introducing oxygen into said slurry sample or said headspace gases;
   computer means responsive to said sensor means for maintaining a constant oxygen concentration in said slurry sample or said headspace gases by controlling said external oxygen source;
   means for measuring and monitoring the oxygen flow from said computer means to determine the oxygen uptake; and,
   means for agitating said slurry sample.

2. The respirometer as defined in claim 1 wherein said means responsive to said sensor means for maintaining a constant oxygen concentration comprises a computer controlled oxygen supply valve in fluid flow communication with said external source of oxygen.

3. The respirometer as defined in claim 1 wherein said sensor means comprises an electronic oxygen sensor inserted into said headspace.

4. The respirometer as defined in claim 1 wherein said sensor means comprises an electronic oxygen probe inserted into said slurry.

5. The respirometer as defined in claim 1 wherein said sensor means comprises an electronic oxygen sensor inserted into said headspace, and an electronic oxygen probe inserted into said slurry.

6. An on-line respirometer comprising:
   an enclosed reaction vessel for simultaneously containing a slurry sample and headspace gases, said slurry sample comprising a mixture of microorganisms and either wastewater or chemical solution;
   means for continuously delivering a flow of microorganisms into said vessel;
   means for continuously delivering a flow of wastewater or chemical solution into said vessel;
   flushing means for establishing a predetermined mixture of headspace gases and for purging undesirable gases from said headspace;
   venting means for discharging headspace gases in response to said flushing means and for discharging slurry in response to said wastewater or chemical solution delivery means;
   sensor means for determining the concentration of oxygen in said headspace gases;
   an external source of pure oxygen for introducing pure oxygen into said headspace gases;
   computer means responsive to said sensor means for maintaining a constant oxygen concentration in said headspace gases by controlling said external oxygen source;
   means for measuring and monitoring the oxygen flow from said computer means to determine the oxygen uptake; and
   means for agitating said slurry sample.

7. The respirometer as defined in claim 6 wherein said computer means responsive to said sensor means for maintaining a constant oxygen concentration in said headspace gases comprises a computer controlled oxygen supply valve in fluid flow communication with said external source of pure oxygen.

8. The respirometer as defined in claim 6 wherein said sensor means comprises an electronic oxygen sensor inserted into said headspace.

9. An on-line respirometer comprising:
   an enclosed reaction vessel for simultaneously containing a slurry and headspace gases, the slurry sample comprising a mixture of a microorganism culture and either wastewater or a chemical solution;
   means for continuously delivering a flow of microorganisms into said vessel;
   means for continuously delivering a flow of wastewater or chemical solution into said vessel;
   flushing means for establishing a predetermined mixture of headspace gases and for purging undesirable gases from said headspace;
   venting means for discharging headspace gases in response to said flushing means and for discharging slurry in response to said wastewater or chemical solution delivery means;

sensor means for determining the concentration of oxygen in said slurry sample;

an external source of pure oxygen for introducing pure oxygen into said slurry sample;

means responsive to said sensor means for maintaining a constant oxygen concentration in said slurry sample by controlling said external oxygen source;

means for measuring and monitoring the oxygen flow from said responsive means to determine the oxygen uptake; and, means for agitating said slurry sample.

10. The respirometer as defined in claim 9 wherein said means responsive to said sensor means for maintaining a constant oxygen concentration in said slurry sample comprises a computer controlled oxygen supply valve in fluid flow communication with said external source of pure oxygen.

11. The respirometer as defined in claim 9 wherein said sensor means comprises an electronic oxygen probe inserted into said slurry.

12. An on-line respirometer for determining the oxygen uptake of a respiring sample, said respirometer comprising:

an enclosed reaction vessel for simultaneously containing a culture slurry and headspace gases;

means for continuously introducing said respiring sample into said vessel to form said slurry;

means for monitoring the flow of said respiring sample into said vessel;

flushing means for establishing a predetermined mixture of headspace gases and for purging undesirable gases from said headspace;

venting means for discharging headspace gases in response to said flushing means and for discharging slurry in response to said wastewater or chemical solution delivery means;

sensor means for determining the concentration of oxygen in said headspace gases;

an external source of pure oxygen for introducing pure oxygen into said headspace gases;

means responsive to said sensor means for maintaining a constant oxygen concentration in said headspace gases or said slurry;

means for measuring and monitoring the oxygen flow from said oxygenation means to determine the oxygen uptake; and, means for agitating said slurry.

13. The respirometer as defined in claim 12 wherein said oxygenation means comprises:

a compressed oxygen cylinder, a system control computer, and an oxygen supply valve.

14. The respirometer as defined in claim 12 wherein said oxygenation means comprises:

an electrolytic cell, a system control computer, and an oxygen supply valve.

15. The respirometer as defined in claim 12 wherein said oxygenation means comprises:

a hydrogen peroxide injection system, a system control computer, and a hydrogen peroxide supply valve.

16. The respirometer as defined in claim 12 wherein said sensor means comprises an electronic oxygen sensor inserted into said headspace.

17. The respirometer as defined in claim 12 wherein said sensor means comprises an electronic oxygen probe inserted into said slurry.

18. The respirometer as defined in claim 12 wherein said sensor means comprises:

an electronic oxygen sensor inserted into said headspace, and;

an electronic oxygen probe inserted into said slurry.

19. The respirometer as defined in claim 12 wherein said computer means electronically controls a valve to selectively vary the oxygenation means rate in response to commands from said computer.

20. A method for determining the oxygen uptake of a respiring sample, said method comprising the steps of:

providing an enclosed reaction vessel for containing a culture slurry comprising a mixture of microorganisms and wastewater or chemical solution and a headspace comprising headspace gases;

introducing said respiring sample into said vessel to form said slurry;

introducing a predetermined mixture of headspace gases into said vessel;

agitating said slurry;

flushing undesirable gases from said headspace;

measuring the concentration of oxygen in said headspace gases;

measuring the concentration of dissolved gases in said slurry;

adding pure oxygen to said reaction vessel in response to said measuring steps to maintain a constant oxygen concentration in said headspace gases or in said culture slurry; and, directly monitoring oxygen flow in said adding step and equating said flow to oxygen uptake.

21. The method of claim 20 wherein gas containing any preset oxygen content is used as a flushing gas to maintain oxygen concentration in the vessel at a level different from the concentration found in air.

22. The method of claim 20 wherein oxygen, air, or gas containing any preset oxygen content is used to flush the undesirable gaseous byproducts from said headspace.

23. The method of claim 20, wherein the headspace gas composition is maintained by the incremental addition of pure oxygen.

24. A method for determining the oxygen uptake of a respiring sample, said method comprising the steps of:

providing an enclosed reaction vessel for containing said respiring sample and a headspace comprising headspace gases;

introducing said sample into said vessel;

introducing a predetermined mixture of headspace gases into said vessel;

flushing undesirable gases from said headspace;

measuring the concentration of dissolved gases in said headspace;

adding pure oxygen to said headspace in response to said measuring step to maintain a constant oxygen concentration, and, directly monitoring oxygen flow in said adding step and equating said flow to oxygen uptake.

25. The method of claim 24 wherein gas containing any preset oxygen content is used as a flushing gas to maintain oxygen concentration in the vessel at a level different from the concentration found in air.

26. The method of claim 24 wherein oxygen, air, or gas containing any preset oxygen content is used to flush the undesirable gaseous byproducts from said headspace.

27. The method of claim 24 wherein the headspace gas composition is maintained by the incremental addition of pure oxygen.

* * * * *